(12) United States Patent
Avinash et al.

(10) Patent No.: US 6,942,621 B2
(45) Date of Patent: Sep. 13, 2005

(54) METHOD AND APPARATUS FOR DETECTING WEAK PHYSIOLOGICAL SIGNALS

(75) Inventors: Gopal B. Avinash, New Berlin, WI (US); Cherik Bulkes, Sussex, WI (US)

(73) Assignee: GE Medical Systems Information Technologies, Inc., Milwaukee, WI (US)

( * ) Notice: Subject to any disclaimer, the term of this patent is extended or adjusted under 35 U.S.C. 154(b) by 591 days.

(21) Appl. No.: 10/192,995

(22) Filed: Jul. 11, 2002

(65) Prior Publication Data

US 2004/0010210 A1 Jan. 15, 2004

(51) Int. Cl.[7] ............................ A61B 5/02; A61B 5/11
(52) U.S. Cl. ........................... 600/481; 600/595
(58) Field of Search ......................... 600/481, 587, 600/595, 529, 534

(56) References Cited

U.S. PATENT DOCUMENTS

| | | | | |
|---|---|---|---|---|
| 3,991,365 A | * | 11/1976 | Takeuchi | 600/453 |
| 4,086,917 A | * | 5/1978 | Burks et al. | 600/453 |
| 4,143,650 A | * | 3/1979 | Hatke | 600/453 |
| 5,524,631 A | * | 6/1996 | Zahorian et al. | 600/511 |
| 5,620,003 A | * | 4/1997 | Sepponen | 600/595 |
| 5,987,983 A | | 11/1999 | Ariav et al. | 73/488 |
| 5,989,193 A | * | 11/1999 | Sullivan | 600/534 |
| 6,030,347 A | * | 2/2000 | Nakamura et al. | 600/595 |
| 6,450,957 B1 | * | 9/2002 | Yoshimi et al. | 600/534 |

* cited by examiner

*Primary Examiner*—Eric F. Winakur
(74) *Attorney, Agent, or Firm*—Fletcher Yoder

(57) ABSTRACT

A method and apparatus are provided for measuring a weak physiological signal in the presence of stronger signals. The method and apparatus utilize motion sensing devices placed on or about the patient to obtain a motion data set from each motion sensing device describing the aggregate detected motion. The data sets are synchronized and then used to solve a set of simultaneous equations which allows for the separation of the various motion components which may include such components of interest as fetal heart motion.

32 Claims, 6 Drawing Sheets

FIG. 5
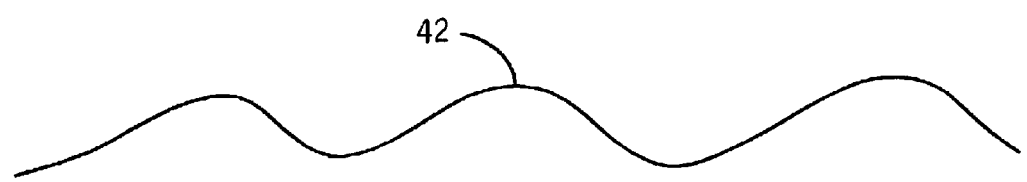
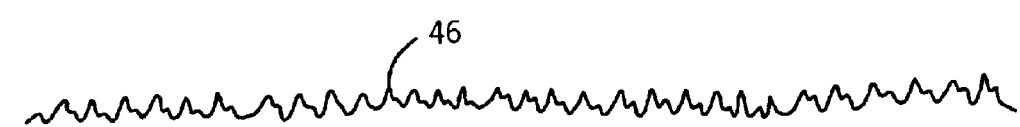
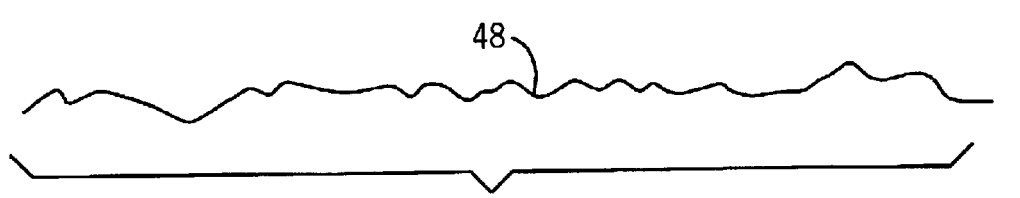
FIG. 6

FIG. 8
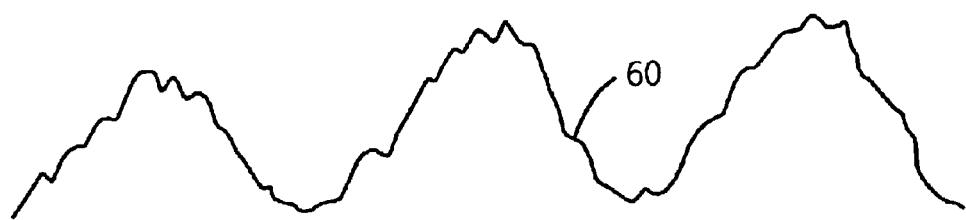
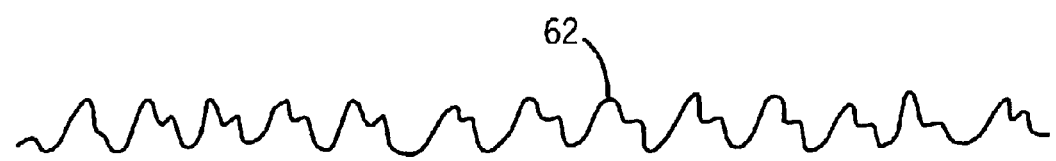
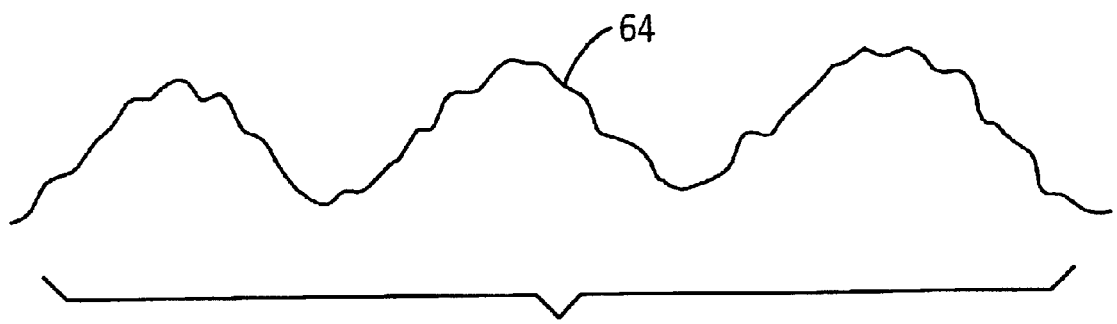
FIG. 9

METHOD AND APPARATUS FOR DETECTING WEAK PHYSIOLOGICAL SIGNALS

BACKGROUND OF THE INVENTION

The present invention relates generally to the field of physiological monitoring, particularly to the detection and monitoring of weak physiological signals in the presence of stronger signals of either physiological or non-physiological origin. Specifically, the invention relates to the separation of signals by resolving multiple equations describing data derived from multiple sensors.

In the field of physiological monitoring it is often desirable to measure a particular signal which may be obscured or confounded by additional, stronger, signals. The stronger signals may be dissimilar from the signal of interest, such as the signal attributable to equipment-induced vibration when measuring heart motion. In some cases, though, the signal may be similar to the signal of interest but of a much greater scale, such as maternal heart motion compared to fetal heart motion. In either case, it may be desirable to detect and monitor the weaker signal.

For example, it may be desirable to determine the fetal heart rate or the waveform associated with fetal heart beat to check for the presence of abnormalities or defects within the developing fetus. However, the fetal heart motion is typically obscured by the mother's respiration and heart movements. The additional movements affect the acquisition and quality of the desired fetal heartbeat data. Though accelerometers and other motion-sensitive detectors can collect data containing information on fetal heart motion, the information will be confounded, if not completely lost, in the presence of stronger, maternal physiological noise.

In such cases, increasing or adjusting the sensitivity of the detector is not a viable solution because the relative strength of the signal is the source of the problem, not the sensitivity of the detector. In the fetal heart monitoring example, the maternal heart motion and maternal respiration will always exceed the fetal heart motion in magnitude. Typically, maternal heart motion will be substantially greater than fetal heart motion. Therefore, a system for monitoring fetal heart motion must be able to separate the fetal heart motion from the stronger components of detected motion such as maternal heart motion, maternal respiration, and non-periodic motion components attributable to the movement of the fetus or mother.

Maternal respiration may be separated from the other responses due to its lower frequency content, which is separable by highpass filtering. However, due to their similarity, maternal and fetal heart motion components typically cannot be separated from one another based on frequency information alone. Therefore, point measurements from a single sensor are inadequate for separating these heart motion components.

Other situations exist where it may be desirable to detect and monitor a weak physiological signal in the presence of a much stronger non-physiological signal. For instance, medical equipment or mechanical devices may produce significant vibration which can obscure a weaker, physiological signal, such as heart motion. In such cases the heart motion and non-physiological vibration may be confounded, making detection and monitoring of the physiological signal impractical using point measurements from a single sensor.

There is a need, therefore, for an improved technique for detecting and monitoring weak physiological signals, such as fetal heart motion, in the presence of stronger physiological and non-physiological signals. To address the drawbacks in heretofore known systems, there is a particular need for a technique which can be employed in a straightforward manner to allow a relatively weak set of signals to be discerned from relatively stronger signals associated with other physiological signals or with non-physiological signals.

BRIEF DESCRIPTION OF THE INVENTION

The invention provides a novel technique for monitoring confounded or obscured physiological signals, such as fetal heart motion, in the presence of stronger physiological signals. The technique may utilize multiple sensors to obtain simultaneous data points which may be used to solve a series of simultaneous equations. The solution of the equations allows the motion components, such as fetal heart motion, maternal heart motion, maternal respiration and other, non-periodic motion, to be separated and analyzed. The technique may, for example, use at least two sensors, depending on the number of signals which must be separated. The sensors themselves may be any type of motion sensitive detector, such as an accelerometer.

The data points obtained by the multiple sensors are first synchronized, typically by a calibration routine applied prior to data collection, such that the respective data points obtained by each sensor correspond in time to one another. Once synchronization is achieved, there should exist multiple data points for each point in time. These multiple data points may then be used to solve the simultaneous equations describing the detected motion components, thereby allowing the discernment of all of the physiological signals, including those weaker signals which would typically be obscured. The simultaneous equations may be solved by any means typically used to solve multiple equations using multiple data sets, including tensor analysis. The present technique thereby allows an array or set of sensitive motion detectors to be used and the motion components associated with a relatively weak motion to be discerned in the presence of motion components associated with much stronger motions.

In accordance with one aspect of the present technique, a method is provided for monitoring fetal heart motion. Motion sensing devices are disposed on or about abdomen of a pregnant woman and are then calibrated to determine a synchronization adjustment for each motion sensor. Each motion sensor then collects a data set and the data sets are synchronized using the previously obtained synchronization adjustment for each motion sensor. The synchronized data sets are then used to solve a set of simultaneous equations in which one of the variables represents the fetal heart motion.

In accordance with another aspect of the present technique, a method is provided for monitoring fetal heart motion. Motion sensing devices are disposed on or about abdomen of a pregnant woman. Each motion sensing device collects a motion data set and the sets are then synchronized. The synchronized motion data sets are then used to solve a set of simultaneous equations, one equation being present for each motion sensing device, thereby determining a fetal heart motion component of the data sets In accordance with another aspect of the present technique, a system is provided for monitoring fetal heart motion. The system includes a sensor array which possesses motion sensitive devices and a signal acquisition circuit which receives a signal from each motion sensitive device. Each signal describes an aggregate motion detected by the motion sensitive device. The system also includes a signal analysis circuit which receives the signals from the signal acquisition circuit. The signal analysis circuit synchronizes the signals and then uses the synchronized signals to solve a set of simultaneous equations, one variable of which is the fetal heart component of the detected aggregate motion.

In accordance with another aspect of the present technique, a circuit is provided for monitoring fetal heart motion. The physiological monitoring circuit determines a component of an aggregate motion data which is attributable to fetal heart motion. The fetal heart motion component is determined by solving a set of simultaneous equations using a plurality of synchronized motion data sets, there being a number of synchronized motion data sets equal to the number of simultaneous equations.

In accordance with another aspect of the present technique, a system is provided for monitoring fetal heart motion. The system includes a sensor array which possesses motion sensitive devices and a signal acquisition circuit which receives a signal from each motion sensitive device. Each signal describes an aggregate motion detected by the motion sensitive device. The system also includes a signal analysis circuit which receives the signals from the signal acquisition circuit. The signal analysis circuit also possesses means for synchronizing the signals and means for solving a set of simultaneous equations using the synchronized signals, one variable of which is the fetal heart component of the detected aggregate motion.

BRIEF DESCRIPTION OF THE DRAWINGS

The foregoing and other advantages and features of the invention will become apparent upon reading the following detailed description and upon reference to the drawings in which:

FIG. 5 is a composite readout of detected physiological motion;

FIG. 6 is a readout of the individual motion components displayed as a composite in FIG. 5;

FIG. 8 is a composite readout of detected motion; and

FIG. 9 is a readout of the individual motion components displayed as a composite in FIG. 8.

DETAILED DESCRIPTION OF SPECIFIC EMBODIMENTS

Figure 1:
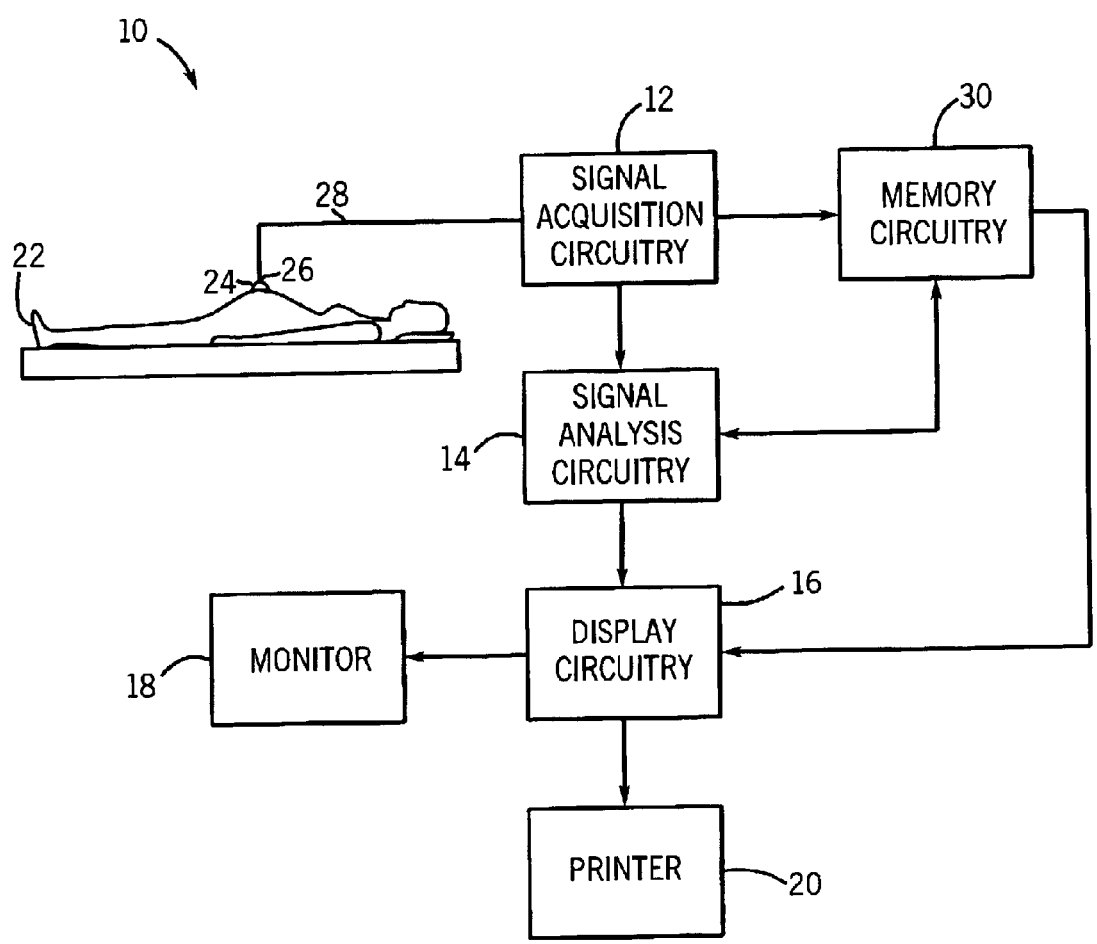
FIG. 1 is a diagrammatic representation of a physiological motion detection system implementing certain aspects of the present monitoring technique.

Turning now to the drawings, and referring first to FIG. 1, a physiological motion detecting system 10 is illustrated diagrammatically as including signal acquisition circuitry 12, signal analysis circuitry 14, and display circuitry 16. The display circuitry 16 is in turn connected to display devices, such as a monitor 18 or a printer 20, which ultimately provide as operator with motion data in a usable format. It is to be understood that the terms "circuit" and "circuitry" are to be construed broadly and any reference to a circuit or to circuitry is meant to cover the hardware, software, or combination of hardware and software which performs or enables the described process The signal acquisition circuitry 12 obtains data points from a patient 22 by means of a sensor array 24 comprising at least one, and typically three or four, motion sensors. The number of sensors needed is ultimately determined by the number of signals to be distinguished and the A mount and type of information needed to identify the signals of interest. Where a plurality of sensors are utilized, the sensors of the sensor array 24 are typically spaced apart and are typically of a type capable of detecting internal physiological motion, such as a heartbeat. Typically, in instances where the measure of fetal heart motion is desired, the sensor array 24 are placed upon the abdomen of the mother, here depicted as patient 22.

If physiological signals are to be detected and monitored, the sensor array 24 may be configured as a pad in which the sensors were embedded or otherwise predisposed such that their relative positions were fixed. However, where desired, sensor array 24 might also consist of unfixed sensors on wire leads which might be positioned by an operator. Whether the sensor array 24 is configured with a fixed or unfixed sensor arrangement, the sensor leads are aggregated at a junction 26 and the collected data is thereby passed to the signal acquisition circuitry 12 by means of a connection wire 28.

The data received by the signal acquisition circuitry 12 is then sent to the signal analysis circuitry 14 where data synchronization occurs. The synchronization step determines the delay between the occurrence of an event and the recognition of that event by the sensor. This delay may be used to compare a sensor calibration factor. The sensor calibration factor may also compensate for signal strength so that the various signals appear equally strong. The output from each sensor is then adjusted by the respective sensor's calibration factor to synchronize the timing and strength of the various output signals. While the distance between a sensor and an event constitutes an important aspect of that sensor's calibration factor, intervening physiological structures, i.e. bones and organs, may also contribute to the factor.

The signal analysis circuitry 14 also comprises circuits or programs which solve a system of simultaneous equations using the synchronized data such that the acquired data set may be broken into its constituent components. In particular, in an exemplary implementation for detecting fetal cardiac activity, for each sensor, at any instant of time, t, the detected signal, S, is defined by the following equation:

$$S(t)=(a)(MR(t))+(b)(MH(t))+(c)(FH(t))+(d)(OT(t)) \quad (1)$$

where a, b, c, and d are distant dependent scalar factors, MR is maternal respiration, MH is maternal heart motion, FH is fetal heart motion, and OT is other motion including the non-periodic motion of the mother and the fetus. The set of simultaneous equations, therefore, consists of the equations associated with each sensor.

In addition, memory circuitry 30 may be included in the motion detecting system 10 so that data collected by the signal acquisition circuitry 12 or data generated by the signal analysis circuitry 14 may be stored for future reference. Similarly, the signal analysis circuitry 14 and the display circuitry 16 may retrieve information from the memory circuitry 30 for processing or display respectively. For purposes of the following discussion, the function or use of the memory circuitry 30 is assumed to be transparent to the operator and to the associated circuitry.

Figure 2:
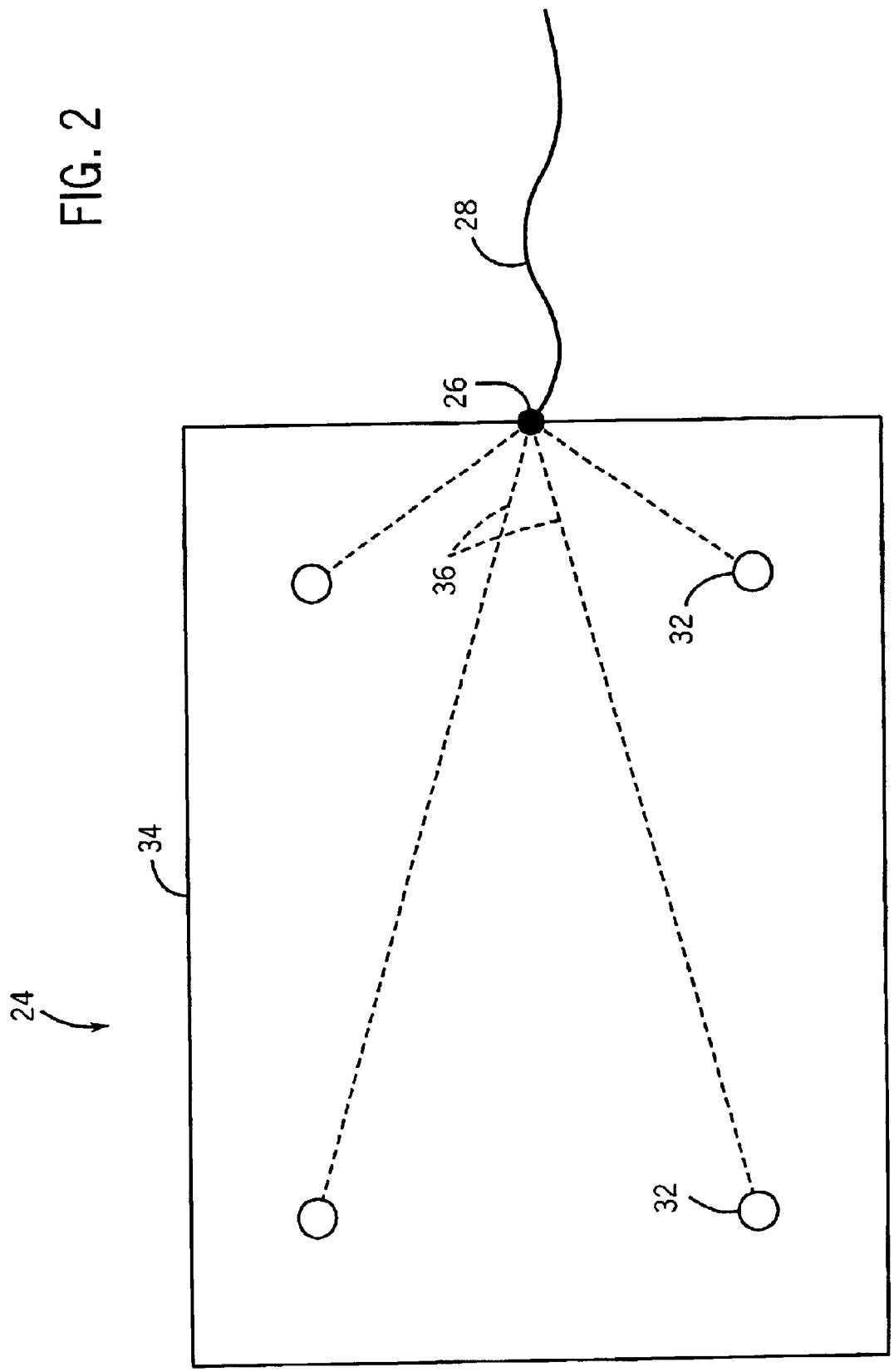
FIG. 2 is a diagrammatic representation of a monitoring pad implementing certain aspects of the present monitoring technique.

Referring now to FIG. 2, a diagrammatic representation of one possible configuration of the sensor array 24 is depicted. The depicted configuration is optimized for the detection of physiological signals, such as fetal heart motion. As depicted in FIG. 2, the sensor array 24 includes four motion sensing devices 32 disposed within a pad 34 or other contact surface. Lead wires 36, here illustrated as dashed lines, are disposed within or along the pad 34 and serve to connect the motion sensing devices 32 with the connection wire 28 at the junction 26. When disposed with a pad 34, the relative positions of motion sensing devices 32 is set, allowing the calibration of the sensor array 24 prior to placement on the patient 22. Typically a known signal is used to calibrate the sensors located on the pad prior to placing the pad upon the patient. In particular, the distance-dependent scalar factors, a, b, c, and d, of equation (1) can be determined prior to placement of the pad 34 upon the patient 22 because the distances between the motion sensing devices 32 are fixed.

Alternatively, the motion sensing devices 32 need not be disposed with a pad 34 or other fixed structure. In such an alternate embodiment, the operator might simply place the motion sensing devices 32 upon the patient 22 in the vicinity of the area of interest. The motion sensing devices 32 would still remain connected to the junction 26 by the connecting lead wires 36. In such a case, no calibration is generally carried out until after the operator places the motion sensing devices upon the patient. After the placement of the motion sensing devices 32 upon the patient 22, a calibration step involving a known signal would be performed to determine the distance-dependent scalar factors, a, b, c, and d of equation (1). The calibration step could be either manual or automated, and would provide the relative distance information to allow the calculation of the distance-dependent scalar factors a, b, c, and d.

Figure 3:
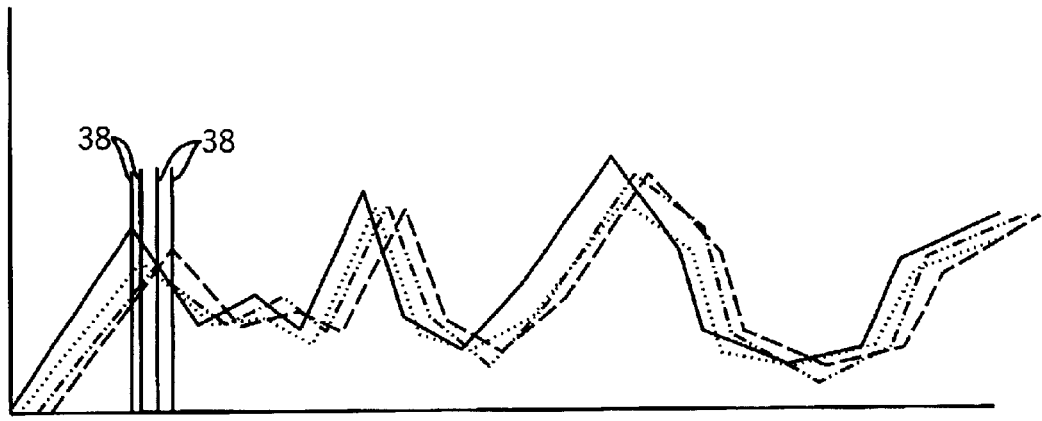
FIG. 3 is an unsynchronized readout of physiological motion data points collected by multiple sensors.
Figure 4:
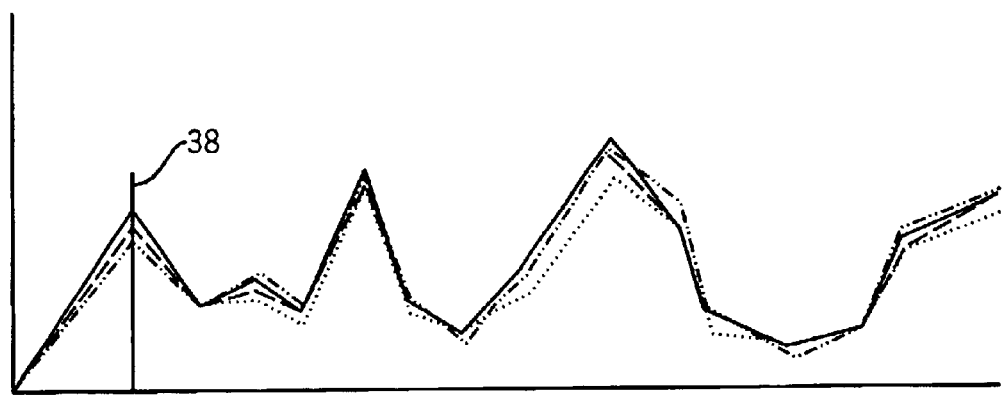
FIG. 4 is a synchronized readout of physiological motion data points collected by multiple sensors.

Once the sensor array 24 has been placed upon the patient 22, the signal acquisition circuitry 12 will begin collecting motion data through the attached sensor array 24 with one set of data points being collected for each motion sensing device 32. These acquired data sets are then passed to the signal analysis circuitry 14 where the data sets are synchronized using the calibration information, i.e. the distance scalar factors a, b, c, and d of equation (1). Referring to FIG. 3, an example of four unsynchronized data sets is depicted. The lack of synchronization may be due to the different distances and different intervening physiological structures between the motion sensing devices 32 and the signal sources. Once the calibration data is used to process the acquired data sets, however, the data sets may be synchronized so that a motion event is represented as occurring at the same point in time on all four synchronized data sets, as seen in FIG. 4. Motion event 38 is represented on FIGS. 3 and 4 to demonstrate the synchronization.

The signal analysis circuitry 14 next uses the information contained within the acquired data sets to solve the set of simultaneous equations consisting of the signal equations, i.e. equation (1), associated with each of the motion sensing devices 32. In this manner the individual components of the aggregate motion can be discerned, allowing weaker components, such as fetal heart motion (FH), to be observed. This can be observed in FIG. 5, which depicts an aggregate motion line 40. The components of the aggregate motion line 40 are depicted beneath it as maternal respiration line 42, maternal heart motion line 44, fetal heart motion line 46, and other non-periodic motion line 48. The motion component comprising the fetal heart motion line 46 can be seen to convey useful diagnostic information such as fetal heart rate and the general waveform associated with fetal heartbeat.

In an alternative embodiment, the sensor array 24 may include fewer motion sensing devices 32, as opposed to the four depicted in FIG. 2, if other means are available for solving for one of the variables being monitored. For instance, maternal respiration has a lower frequency than the other motion components and can be separated from them by highpass filtering of the individual sensor signals. If such filtering is employed, maternal respiration need not be solved for, leaving only three variables, MH 44, FH 46, and OT 48, which must be determined. In this embodiment, only three equations are necessary to solve for these three variables and, therefore, only three motion sensing devices 32 are used in sensor array 24. In other words, there are generally as many simultaneous equations as there are unknown variables, each equation being produced by a separate motion sensing device 32.

The simultaneous equations themselves may be solved by a variety of techniques known to those skilled in the art. Any of the known techniques for solving for multiple variables using multiple sets of data points may be utilized. One preferred technique suitable for solving such simultaneous multi-variate equations is tensor analysis, though related linear algebraic techniques may be utilized as well.

After resolution of the simultaneous equations, the signal analysis circuitry 14 may perform an additional validation step. The validation technique may take various forms. However, one suitable technique is to analyze the results relative to the other non-periodic motion line 48. Obviously, the other non-periodic motion line 48 may be of various forms and shapes, but its magnitude may be used generally to determine that calculations are valid. Solutions in which the magnitude of the non-periodic component 48 exceeds the value of the periodic components suggest that the calculations may be invalid for those times in question, perhaps due to patient movement, dislocation of the sensor array 24, and so forth.

Figure 7:
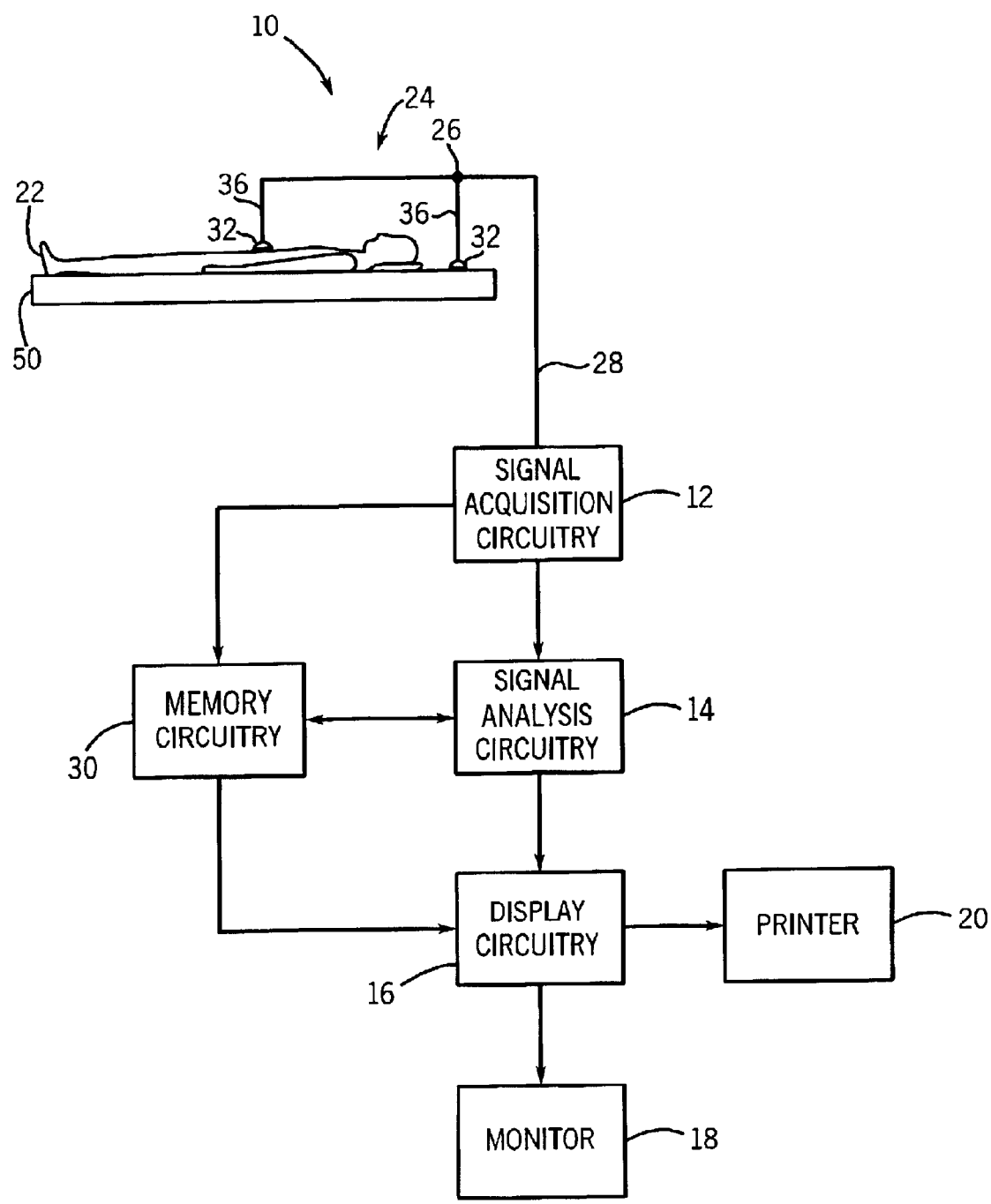
FIG. 7 is a diagrammatic representation a motion detection system implementing certain aspects of the present monitoring technique.

One skilled in the art will recognize that alternative embodiments of the present technique exist whereby a weak physiological signal may be discerned in the presence of stronger non-physiological signals or noise, such as those produced by various types of medical equipment or related devices. Where only two signals, i.e. a physiological and non-physiological signal, are being separated, as few as two motion sensing devices 32 may be employed, as depicted in FIG. 7. Such an embodiment might be desirable where a strong and persistent non-physiological signal is transmitted from or through a table or gurney supporting a patient 22 and interferes with the detection and monitoring of a weaker physiological signal, such as heart motion.

As depicted in FIG. 7, in an exemplary application of this type, a motion sensing device 32 may be placed on the patient 22, preferably near the source of the physiological signal. A second motion sensing device 32 may be placed upon the source or transmitter of the non-physiological signal, such as table 50. The physiological and non-physiological signals may be processed as described above to separate the respective signals. In this manner a composite signal 60, as depicted in FIG. 8, may be separated into its components, physiological signal 62 and non-physiological signal 64, as depicted in FIG. 9. In this manner the physiological signal 62 of interest may be monitored even in the presence of an otherwise stronger non-physiological signal 64.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A method for detecting a physiological signal of interest comprising:
   disposing two or more motion sensing devices on or about a patient;
   calibrating the two or more motion sensors such that a synchronization adjustment is determined for each motion sensor;
   collecting a data set from each motion sensor;
   synchronizing the data sets using the synchronization adjustment; and
   using the synchronized data sets to solve a set of simultaneous equations in which one variable represents the physiological signal of interest.

2. The method of claim 1, wherein the physiological signal of interest is fetal heart motion.

3. The method of claim 2, wherein disposing a plurality of motion sensing devices comprises placing a pad to which motion sensors have been associated upon the patient.

4. The method of claim 2 further comprising determining at least one of a fetal heart rate and a fetal heart waveform.

5. The method of claim 1, wherein the plurality of motion sensing devices is at least two motion sensing devices.

6. The method of claim 1, wherein solving the set of simultaneous equations comprises performing a tensor analysis upon the plurality of data sets.

7. The method of claim 1, further comprising checking the validity of the solution to the simultaneous equations.

8. The method of claim 7, wherein checking the validity comprises analyzing a non-periodic component of the plurality of data sets.

9. A method for monitoring fetal heart motion comprising:
   collecting a motion data set from each of two or more motion sensing devices disposed on or about a patient;
   synchronizing the motion data sets; and
   solving a set of simultaneous equations to determine two or more motion components of the synchronized motion data sets related to fetal heart motion.

10. The method of claim 9, wherein one of the determined motion components is attributable to a fetal heartbeat.

11. The method of claim 10, further comprising determining a fetal heart rate from the fetal heartbeat component.

12. The method of claim 10, further comprising determining a fetal heart waveform from the fetal heartbeat component.

13. The method of claim 9, wherein the number of simultaneous equations is equal to the number of synchronized motion data sets and is greater than or equal to the number of motion components.

14. The method of claim 9, further comprising disposing the two or more motion sensing devices upon a pad.

15. The method of claim 9, wherein solving the set of simultaneous equations comprises performing a tensor analysis upon the synchronized motion data sets.

16. The method of claim 9, further comprising checking the validity of the solution to the simultaneous equations.

17. The method of claim 16, wherein checking the validity comprises analyzing a non-periodic component of the synchronized motion data sets.

18. A physiological monitoring system for monitoring a physiological signal of interest comprising:
   a sensor array comprising two or more motion sensitive devices;
   a signal acquisition circuit configured to receive a signal from each motion sensitive device such that each signal describes an aggregate motion; and
   a signal analysis circuit configured to receive the signals from the signal acquisition circuit, to synchronize the signals, and to solve a set of simultaneous equation using the synchronized signals such that two or more components of the aggregate motion are discerned, wherein at least one component is the physiological signal of interest.

19. The physiological monitoring system of claim 18, wherein the physiological signal of interest is a motion component attributable to a fetal heartbeat.

20. The physiological monitoring system of claim 19, wherein the signal analysis circuit determines a fetal heart rate from the motion component attributable to a fetal heartbeat.

21. The physiological monitoring system of claim 19, wherein the signal analysis circuit determines a fetal heart waveform from the motion component attributable to a fetal heartbeat.

22. The physiological monitoring system of claim 18, wherein the sensor array comprises a pad upon which the two or more motion sensitive devices are disposed.

23. The physiological monitoring system of claim 18, wherein the signal analysis circuit solves the set of simultaneous equations by tensor analysis.

24. A physiological monitoring circuit comprising an input for receiving an aggregate motion data set and analysis circuitry configured to separate a motion component of interest from the aggregate motion data set by solving a set of simultaneous equations using two or more synchronized motion data sets, wherein the motion component of interest is attributable to a physiological source.

25. The physiological monitoring circuit of claim 24, wherein the motion component of interest is attributable to a fetal heartbeat.

26. The physiological monitoring circuit of claim 24, wherein the set of simultaneous equations are solved by tensor analysis.

27. The physiological monitoring circuit of claim 24, wherein the aggregate motion data set includes a motion component attributable to a non-physiological source.

28. A physiological monitoring system comprising:
   a sensor array comprising two or more motion sensitive devices;
   a signal acquisition circuit configured to receive a signal from each motion sensitive device wherein each signal describes an aggregate motion; and
   a signal analysis circuit configured to receive the signals from the signal acquisition circuit, and including means for synchronizing the signals and means for solving a set of simultaneous equations using the synchronized signals such that a motion component of interest of the aggregate motion is discerned.

29. The physiological monitoring system of claim 28, wherein the motion component of interest is attributable to a fetal heartbeat.

30. The physiological monitoring system of claim 28, wherein the sensor array comprises a pad upon which the two or more motion sensitive devices are disposed.

31. The physiological monitoring system of claim 28, wherein there are four motion sensitive devices.

32. The physiological monitoring system of claim 28, wherein there are three motion sensitive devices.

* * * * *